(12) United States Patent
Luecke et al.

(10) Patent No.: US 9,279,974 B2
(45) Date of Patent: Mar. 8, 2016

(54) MICROSCOPY SYSTEM AND METHOD

(75) Inventors: Christian Luecke, Oberkochen (DE); Alfons Abele, Schwaebisch Gmuend (DE); Dirk Brunner, Aalen (DE); Frank Rudolph, Aalen (DE); Fritz Straehle, Heubach (DE); Joachim Steffen, Westhausen (DE); Michael Wirth, Aalen (DE)

(73) Assignee: CARL ZEISS MEDITIC AG, Jena (DE)

( * ) Notice: Subject to any disclaimer, the term of this patent is extended or adjusted under 35 U.S.C. 154(b) by 0 days.

(21) Appl. No.: 12/341,581

(22) Filed: Dec. 22, 2008

(65) Prior Publication Data

US 2009/0180178 A1    Jul. 16, 2009

Related U.S. Application Data

(63) Continuation of application No. 10/913,035, filed on Aug. 6, 2004, now Pat. No. 7,468,835.

(30) Foreign Application Priority Data

Aug. 8, 2003    (DE) .................................. 103 36 475

(51) Int. Cl.
| | |
|---|---|
| G02B 21/22 | (2006.01) |
| G02B 21/18 | (2006.01) |
| A61B 3/13 | (2006.01) |
| G02B 21/36 | (2006.01) |
| G02B 21/00 | (2006.01) |
| G02B 7/00 | (2006.01) |

(52) U.S. Cl.
CPC ................ *G02B 21/18* (2013.01); *A61B 3/132* (2013.01); *G02B 21/22* (2013.01); *G02B 21/368* (2013.01); *G02B 7/002* (2013.01); *G02B 21/0028* (2013.01)

(58) Field of Classification Search
CPC ................ G02B 21/18–21/22; G02B 21/0012; G02B 21/0016; G02B 21/0028; G02B 21/025; G02B 21/0052; G02B 21/0072; G02B 21/008; G02B 21/0088; G02B 21/36; G02B 21/365
USPC ......... 359/372–374, 376–378, 388, 831, 834, 359/835; 351/205, 206, 214, 216, 245; 348/79
See application file for complete search history.

(56) References Cited

U.S. PATENT DOCUMENTS

| | | |
|---|---|---|
| 4,710,000 A | 12/1987 | Spitznas et al. |
| 4,786,154 A | 11/1988 | Fantone et al. |
| 4,991,947 A | 2/1991 | Sander et al. |

(Continued)

FOREIGN PATENT DOCUMENTS

| | | |
|---|---|---|
| DE | 3826069 C2 | 2/1990 |
| DE | 3833876 A1 | 4/1990 |

(Continued)

*Primary Examiner* — Thomas K Pham
*Assistant Examiner* — Marin Pichler
(74) *Attorney, Agent, or Firm* — Patent Portfolio Builders PLLC (57) ABSTRACT

A microscopy system method for inspecting a retina of an eye including generating an inverted intermediate image of the retina using an opthalmoscopic lens; detecting a left image of the intermediate image from a left viewing direction and detecting a right image of the intermediate image from a right viewing direction; and displaying an inverted representation of the detected left image to a right eye of a user and displaying an inverted representation of the detected right image to a left eye of the user.

13 Claims, 3 Drawing Sheets

(56) References Cited

U.S. PATENT DOCUMENTS

| | | |
|---|---|---|
| 5,009,487 A | 4/1991 | Reiner |
| 5,227,914 A | 7/1993 | Hanzawa et al. |
| 5,287,219 A | 2/1994 | Hildebrand et al. |
| 5,321,447 A | 6/1994 | Sander et al. |
| 5,331,457 A | 7/1994 | Hanzawa et al. |
| 5,438,456 A | 8/1995 | Grinblat |
| 5,535,060 A | 7/1996 | Grinblat |
| 5,579,156 A | 11/1996 | Faltermeier et al. |
| 5,729,382 A | 3/1998 | Morita et al. |
| 5,867,210 A | 2/1999 | Rod |
| 6,598,972 B2 | 7/2003 | Strahle |
| 2002/0131017 A1 | 9/2002 | Kishida et al. |
| 2003/0165012 A1 | 9/2003 | Straehle et al. |
| 2003/0231285 A1 | 12/2003 | Ferguson |
| 2004/0017607 A1 | 1/2004 | Hauger et al. |
| 2004/0183999 A1 | 9/2004 | Kogawa et al. |

FOREIGN PATENT DOCUMENTS

| | | |
|---|---|---|
| DE | 4012552 A1 | 10/1991 |
| DE | 41 23 279 A1 | 2/1992 |
| DE | 4114646 A1 | 11/1992 |
| DE | 93 01 434.1 U1 | 7/1993 |
| DE | 29505775 U1 | 7/1995 |
| DE | 19517476 A1 | 11/1995 |
| DE | 19718102 A1 | 12/1997 |
| DE | 10140402 A1 | 4/2002 |
| EP | 0662625 A2 | 7/1995 |
| EP | 1191381 A2 | 3/2002 |
| JP | 09318882 A | 12/1997 |
| JP | 10090607 A | 4/1998 |
| JP | 2002350735 A | 12/2002 |
| WO | 91/15150 | 10/1991 |

MICROSCOPY SYSTEM AND METHOD

RELATED APPLICATIONS

This application is a continuation of U.S. patent application Ser. No. 10/913,035, filed Aug. 6, 2004 now U.S. Pat. No. 7,468,835 which claims the benefit of priority application DE 103 36 475.7 filed in Germany on Aug. 8, 2003. The subject matter of both of these applications are incorporated herein by reference.

BACKGROUND OF THE INVENTION

1. Field of the Invention

The invention relates to a microscopy system and method. In particular, the invention relates to a surgical microscopy system of the binocular type and a microscopy method for inspecting a retina of an eye.

2. Brief Description of Related Art

From U.S. Pat. No. 4,786,154 there is known a stereo-microscopy system comprising an objective lens for transforming an object-side imaging beam emerging from an object plane of the objective lens into an image-side imaging beam. A left zoom system and a right zoom system are disposed within the image-side imaging beam. The left zoom system picks up a left beam portion of the image-side imaging beam and supplies that portion with an adjustable magnification to a left ocular of the microscopy system. Similarly, the right zoom system picks up a right beam portion of the image-side imaging beam and supplies that portion with an adjustable magnification to a right ocular of the microscopy system. Two semitransparent mirrors are disposed in each of the left and right beam portions in-between of the respective zoom system and ocular. A first of the two mirrors is used to supply light of the respective beam portion to a camera. Images detected by the camera are supplied to a controller for further processing. The controller supplies the processed images to a display, and light generated by the display is superimposed with the respective beam portion by the second semitransparent mirror. When looking into the oculars, the user may perceive a direct image of the object and a superimposed representation generated by the displays.

The two semitransparent mirrors disposed in the beam paths tend to increase the volume and length of the microscopy system.

From EP 1 191 381 A2 there is known a stereo-microscopy system which is configured to be used for surgery at the human eye and to generate a stereo-microscopic image of a retina of the eye. For this purpose, an opthalmoscopic lens is inserted in a beam path between the objective lens of the microscopy system and the eye under surgery. The opthalmoscopic lens generates an intermediate image of the retina of the eye in the object plane of the objective lens. The intermediate image is an inverted image, and the microscopy system comprises optics for interchanging the stereo channels of the microscopy system and for inverting each of the stereo-images supplied to oculars of the microscopy system.

Such optics also tends to increase the volume and length of the microscopy system.

SUMMARY OF THE INVENTION

The present invention has been accomplished taking the above problems into consideration.

It is an object of the present invention to provide a stereo-microscopy system of a simplified configuration and which is suitable to be used in combination with an opthalmoscopic lens.

It is a further object of the present invention to provide an improved microscopy method for inspecting a retina of an eye.

The foregoing objects are accomplished by providing a microscopy system for generating a magnified stereoscopic image of an object. The microscopy system comprises an objective lens for transforming an object-side beam emerging from an object plane of the objective lens into an image-side beam. Left and right cameras are disposed within the image-side beam to be supplied with light of left and right beam portions of the image-side beam for detecting an image of the object from left and right viewing directions, respectively. The microscopy system further comprises left and right displays for generating representations of the object to be viewed by a left and right eyes, respectively, of a user.

A control system of the microscopy system has first and second modes of operation. In the first mode of operation, the controller supplies an inverted representation of the image detected by the left camera to the right display, and supplies an inverted representation of the image detected by the right camera to the left display.

The invention thus provides a simplified microscopy system to be used in combination with an opthalmoscopic lens and which performs the necessary interchanging of the stereo-channels together with the necessary image inversion. Other than in the conventional system, where the interchanging of the stereo-channels and image inversion is achieved by using complicated optical means, the interchanging of the stereo-channels and image inversion is achieved in the microscopy system according to the present invention by electronic means provided by the controller.

In the second mode of operation, a non-inverted representation of the image detected by the left camera is supplied to the left display, and a non-inverted representation of the image detected by the right camera is supplied to the right display. In the second mode of operation the microscopy system may be used for inspecting an object which is disposed in the object plane of the objective lens. The microscopy system may be switched from the first mode of operation to the second mode of operation, i.e. from an operation involving use of an opthalmoscopic lens to an operation without involving such opthalmoscopic lens, by a switching of the control system and without making it necessary to move optical components into the beam path or out of the beam path.

According to an exemplary embodiment of the invention, the left and right displays are comprised in a head mounted display. The user may then freely move relative to the objective lens while viewing the magnified stereoscopic representation of the object. According to a further exemplary embodiment, the left and right displays are mounted on a support such that the user has the choice of viewing the magnified representation of the object through the displays or viewing directly onto the object or some other point of interest.

According to some embodiments of the invention, the microscopy system further comprises a left ocular and a right ocular which are supplied with light of the left and right beam portions such that the user may also perceive a purely optical stereomicroscopic representation of the object by looking into the oculars. In such embodiments, the microscopy system preferably comprises a beam splitter for supplying light of the left and right beam portions to both the respective ocular and the respective camera.

In an exemplary embodiment herein, the inspection, in the second mode of operation for inspecting the object disposed in the object plane without an opthalmoscopic lens disposed in the beam path, is performed using the optical beam path between the objective lens and the oculars. In the first mode of operation for inspecting the object using the inverting opthalmoscopic lens, the inspection is performed using the representations generated by the displays and superimposed with a beam path towards the oculars, wherein inverted representations of the images detected by the cameras are supplied while interchanging the stereo-channels.

In a further exemplary embodiment herein, the microscopy system comprises a beam switch having a first switching state in which the supply of the beam portions to the oculars is allowed, and a second switching state in which the supply of the beam portions to the oculars is blocked.

According to an exemplary embodiment of the invention, the operation of the beam splitter is synchronized with a switchable illumination system of the microscopy system, wherein the illumination system has a first illumination state in which an illuminating beam is directed towards the inspected object, and a second illumination state in which an illuminating beam is not directed onto the object. In the first mode of operation of the control system the beam path between the objective lens and the oculars is not blocked, wherein the object is not illuminated in this first mode of operation, however. Thus, the user will not perceive the object through the optical beam path when looking into the oculars in the first mode of operation. He will then perceive the representation generated by the displays, which generate inverted representations of the object while interchanging the stereo-channels. Thus, the user will perceive non-inverted representations of the object with a correct stereo base while using the opthalmoscopic lens. The two beam portions are permanently supplied to the cameras. The images of the object are substantially only detected in the second mode of operation of the control system since it is only then that the illumination system illuminates the object with the illuminating beam. In this second mode of operation the direct beam path of the two beam portions towards the oculars is blocked such that the user will not perceive the direct optical inverted image with interchanged stereo-channels when looking into the oculars in the second mode of operation. If necessary, the camera, the display or the corresponding controller may comprise a memory for storing the images detected by the cameras during the second mode of operation where the cameras will detect the images. Representations of the stored images will be supplied to the displays during that time where the illuminating beam is not incident on the object. Such memory may not be necessary if a response time of the display is sufficiently low such that the intensity variations caused by the intermittent illumination of the object are not perceived by the user.

Preferably, the switching between the first and second modes of operation is periodically performed at a sufficiently high frequency such that the user will substantially continuously perceive the inverted representations with interchanged stereo-channels of the object.

The invention further provides a microscopy method for inspecting a retina of an eye, the method comprising: generating an inverted intermediate image of the retina; detecting a left image of the intermediate image from a left viewing direction and detecting a right image of the intermediate image from a right viewing direction; and displaying an inverted representation of the detected left image to a right eye of a user and displaying an inverted representation of the detected right image to a left eye of the user.

BRIEF DESCRIPTION OF THE DRAWINGS

The forgoing as well as other advantageous features of the invention will be more apparent from the following detailed description of exemplary embodiments of the invention with reference to the accompanying drawings, wherein.

DETAILED DESCRIPTION OF EXEMPLARY EMBODIMENTS

In the exemplary embodiments described below, components that are alike in function and structure are designated as far as possible by alike reference numerals. Therefore, to understand the features of the individual components of a specific embodiment, the descriptions of other embodiments and of the summary of the invention should be referred to.

Figure 1:
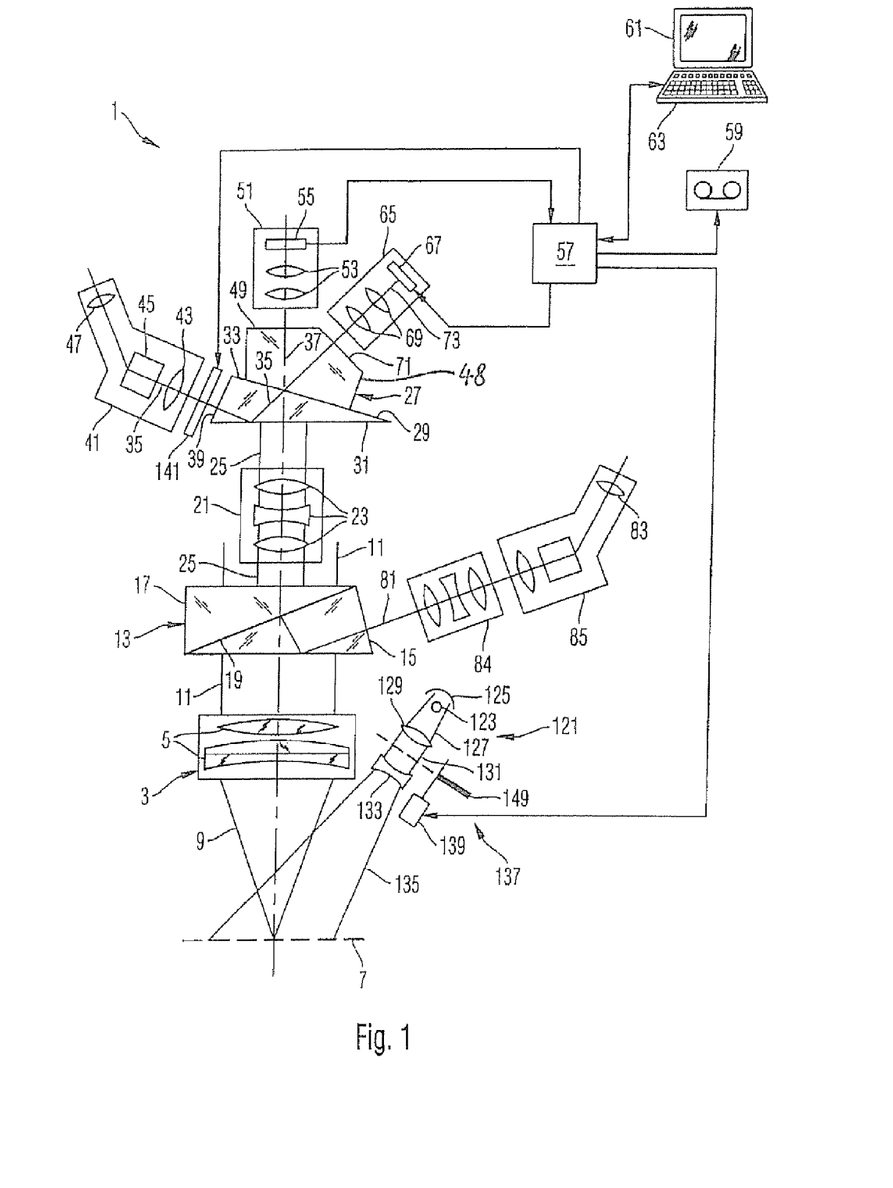
FIG. 1 schematically shows a stereo-microscopy system which may be used in combination with an opthalmoscopic lens, according to a first embodiment of the invention.

FIG. 1 schematically illustrates a microscopy system 1 comprising an objective lens system 3 having plural objective lenses 5 for transforming an object-side imaging beam 9 emerging from an object plane 7 of the objective lens 3 into an image-side imaging beam 11.

A beam splitter arrangement 13 is disposed in the image-side imaging beam 11. The beam splitting arrangement 13 comprises a prism 15 of the Bauernfeind type and having a wedge shaped prism 17 cemented thereon. A splitting of the beam path is generated at an interface 19 of the beam splitting arrangement, wherein a beam path for a main user straightly traverses the interface 19. A pair of zoom system 21 each having plural zoom lenses 23 is disposed in the beam path of the main user downstream of the beam splitter arrangement. Only one of the two zoom systems 21 is visible in FIG. 1 while hiding the other zoom system.

Each of the zoom systems picks up a beam portion 25 of the image-side imaging beam 11 to supply that beam portion 25 to a beam splitting arrangement 27. The beam splitting arrangement 27 comprises a prism 29 of the Bauernfeind type having a first surface 31 facing towards the zoom system 21, wherein the beam portion 25 supplied by zoom system 21 enters prism 29 through the first surface 31. The prism 29 has a second semitransparent surface 33 for splitting the beam path into an ocular beam path 35 and a camera beam path 37, wherein the camera beam path straightly traverses the semitransparent surface 33 and the ocular beam path 35 is reflected from second surface 33. The ocular beam path 35 is then reflected from the first surface 31 of prism 29 by internal total reflection and then emerges from prism 29 by traversing a third surface 39 of prism 29 to enter a body of a tube 41 comprising plural lenses 43 and a beam deflector 45 to supply the ocular beam path to oculars 47. The oculars 47 are pivotable to be adaptable to a distance of the eyes of the user.

The camera beam path 37 traverses the second surface 33 of prism 29 and enters a prism 48 which is joined to prism 29 by cementing. The camera beam path 37 straightly traverses prism 48 and emerges therefrom through a surface 49 to be incident into a camera 51 having a camera adapter optics 53 and a CCD chip 55. Images detected by the CCD chip 55 are read out by a controller 57 to be stored in an archive 59, such as a magnetic tape or other, or to be displayed on a computer display 61 after performing some image processing, if desired. The controller 57 is further configured to supply data to a display 65. The data may comprise the images detected by camera 51, the corresponding image processed images or other data such as data entered by using a keyboard 63. The display 65 comprises a LCD chip 67 and a display optics 69. Light generated by the display 65 enters prism 48 by traversing a surface 71 thereof under such an angle that a beam path 73 of the display is superimposed with the ocular beam path 35 after traversing the second surface 33 of prism 29. When looking into the oculars 47 the user will perceive both the optical image of the object plane 7 supplied by the object-side imaging beam 11 and the corresponding beam portions 25, and the superimposed representations generated by the displays 65.

A beam path 81 reflected by prism 15 of the Bauernfeind type is supplied to oculars 83 for an assistant user to perceive an optical image of object plane 7. A pair of zoom systems 84 and a tube 85 having a similar configuration as zoom system 21 and tube 41 illustrated above are disposed in beam path 81.

Figure 2:
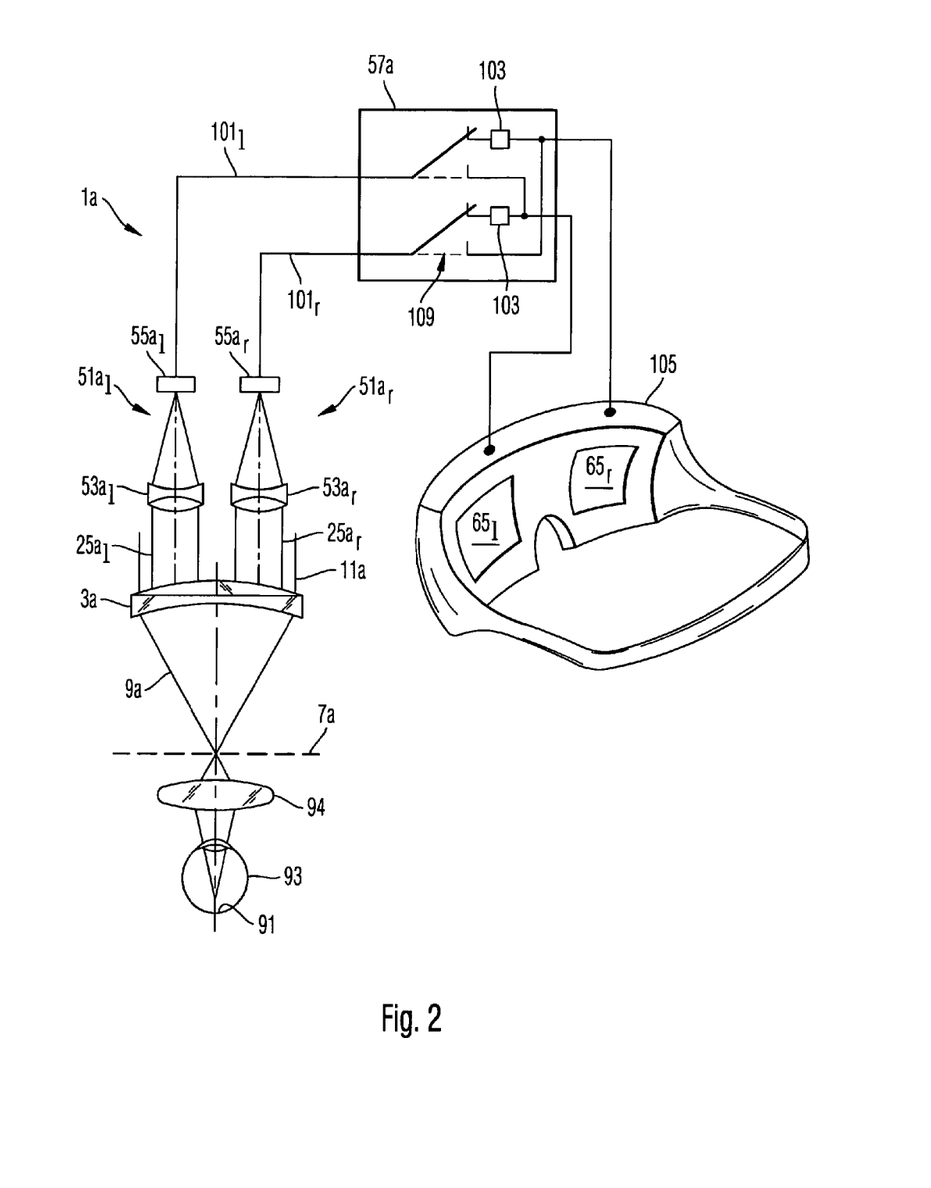
FIG. 2 schematically shows a stereo-microscopy system which may be used in combination with an opthalmoscopic lens, according to a second embodiment of the invention.

FIG. 2 schematically illustrates a microscopy system 1a comprising an objective lens 3a having an object plane 7a.

The objective lens 3a transforms an object-side imaging beam 9a emerging from an object plane 7a into an image-side imaging beam 11a. Two cameras 41al and 41ar are disposed in the image-side imaging beam 11a (the additional character l stands for "left", and the additional character r stands for "right"). The cameras 51al and 51ar each comprise a camera adapter optics 53al,r and a CCD chip 55al,r and detect images of the object plane 7a from left and right viewing directions, respectively. In the embodiment shown in FIG. 2 zoom systems are not disposed in the beam path between the objective lens and the cameras; corresponding zoom systems may be provided, however, for optically changing a magnification of the images detected by cameras 51al,r.

The microscopy system 1a is used for inspecting a retina 91 of an eye 93 and comprises an opthalmoscopic lens 94 generating an intermediate image of retina 91 in the object plane 7a. An example of an opthalmoscopic lens is disclosed in U.S. Pat. No. 4,728,183. The images detected by cameras 51al, 51ar are inverted pseudo-stereoscopic images. This means that the stereo-channels are interchanged and that the left and right and up and down sides of the images are inverted.

The images detected by cameras 51al, 51ar are supplied to controller 57a via data lines 101l, 10r, respectively, transformed by electronic image inverters 103 to have a correct orientation, and supplied to a head mounted display 105. The head mounted display comprises a left display 65l to be viewed with a left eye of the user, and a right display 65r to be viewed by a right eye of the user. The images detected by camera 51al are supplied to display 65r after image inversion, and the images detected by camera 51ar are supplied to display 65l after image inversion, such that the user will perceive a correctly oriented representation of the retina 91 with a correct stereo impression.

If the user intends to inspect an object disposed in the object plane 7a without using the opthalmoscopic lens 94, he will switch the controller 57a to a second mode of operation, wherein a corresponding switch 109 is only schematically indicated in FIG. 2. In the second mode of operation the images detected by camera 51al are supplied to display 65l without being inverted, and the images detected by camera 51a are supplied to display 65r without being inverted.

Figure 3:
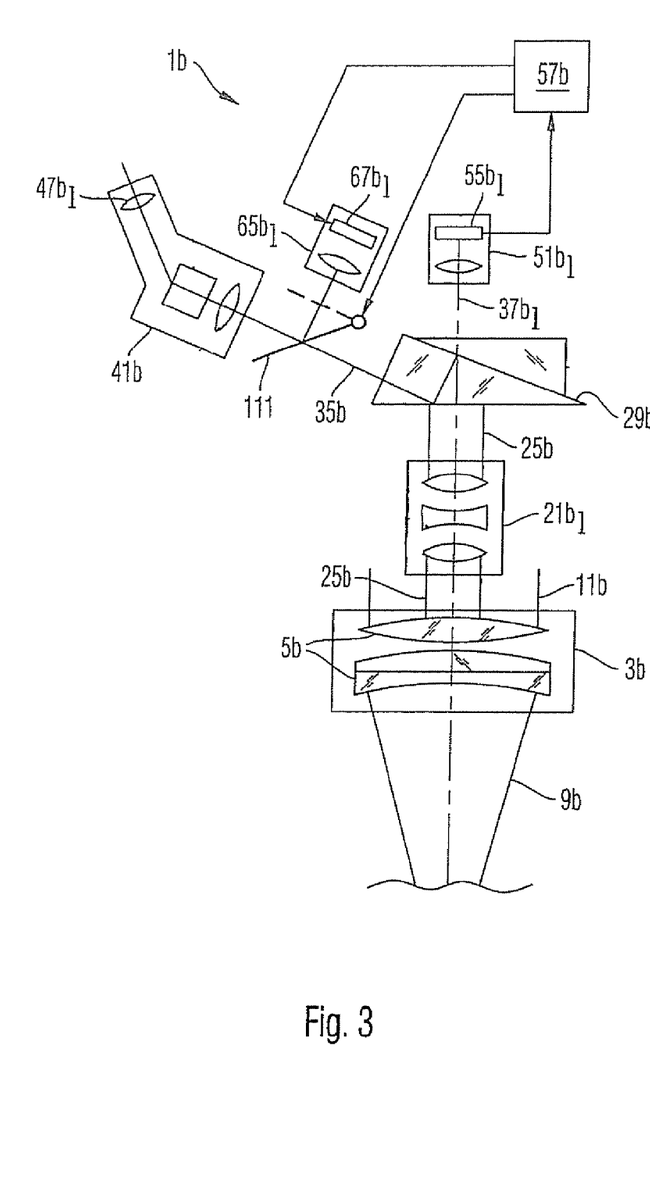
FIG. 3 schematically shows a stereo-microscopy system which may be used in combination with an opthalmoscopic lens, according to a third embodiment of the invention.

FIG. 3 shows a stereo-microscopy system 1b which can be operated in a first mode of operation for inspecting a retina using an opthalmoscopic lens and a second mode of operation for inspecting an object without such opthalmoscopic lens.

The inspection without opthalmoscopic lens is a direct optical inspection wherein an object-side beam 9b is transformed into an image-side beam 11b by an objective lens 3b. A pair of zoom systems picks out a pair of beam portions 25b which are finally supplied to respective oculars 47b. Only one zoom system 21bl is shown in FIG. 3. The two beam portions 25b are split by a prism 29b of the Bauernfeind type. A first portion of the split beams forms an ocular beam path 35b and is supplied to the oculars 47b via a tube arrangement 41b. A second portion of the split beams forms a camera beam path 37b and is supplied to a pair of cameras 51b having a CCD chip 55b, wherein a camera 51bl detects an image of an object plane from a left viewing direction, and a second camera (not shown in FIG. 3) detects an image of the object plane from a right viewing direction.

The images detected by cameras 51b are read out by a controller 57b and supplied to displays 65b having LCD chips 67b for displaying the images.

In the first mode of operation where the opthalmoscopic lens is used for inspection, the images of the displays 65b are superimposed with the ocular beam paths by a hinged mirror 111 which is disposed in the ocular beam paths 53b as indicated by solid lines in FIG. 3b. In this shown position the hinged mirror 111 blocks the light emerging from the object and supplied by the zoom systems 21b towards the oculars. When looking into the oculars 47b the user will perceive the images of the representations generated by the displays 65b wherein the controller 57b has inverted the images detected by cameras 51b and has interchanged the stereo-channels. Thus, the user will perceive an image of a retina through an opthalmoscopic lens (not shown in FIG. 3) with a correct orientation and correct stereoscopic impression.

For inspecting the object without opthalmoscopic lens, the hinged mirror 111 is rotated by a corresponding actuator (not shown in FIG. 3) under the control of controller 57b to a position shown in broken lines in FIG. 3. In such position the mirror 111 does not superimpose the light generated by the displays 65b with the ocular beam path, and the mirror 111 does not block the light emerging from the object and supplied to the oculars 47b through the objective lens 3b, the zoom systems 21b and the beam splitter 29b. The user may directly inspect the object by pure optical imaging, accordingly.

Also the microscopy system 1 is configured for an inspection involving an opthalmoscopic lens. For this purpose, the microscopy system 1 comprises an illumination system 121 comprising a light source 123 and a reflector 125 for generating a light beam 127. A collimator 129 is provided for forming light beam 127 to be a collimated beam 131. A further lens group 133 is provided to transform collimated beam 131 into an illuminating beam 135 suitable for illuminating an object field in object plane 7. The illumination system 121 is schematically illustrated in FIG. 1 such that the illuminating beam 135 is obliquely incident on object plane 7. Other embodiments suitable for opthalmoscopic surgery will use illuminating beams reflected from deflecting mirrors such that the beam is incident onto the object plane under only a small angle relative to the optical axis of the objective lens.

The illuminating system 121 further comprises a chopper 137 having a motor 139 and a chopper wheel 149 having plural chopper blades for alternatingly blocking the illuminating beam 135 and allowing the beam to pass through. A rotating speed and phase of the motor 139 is controlled by controller 57. The object will alternatingly be illuminated and not be illuminated. A beam shutter 141 is disposed in a beam path between the prism 29 of the Bauernfeind type and the tube 41. In a state of the illuminating system 121 where the object is illuminated, the controller switches the light shutter 141 into its light blocking state such that the user will not perceive the optical image of the object when looking into the oculars 47. The cameras 51 will detect an image of the object in such illumination state and the controller 57 will read out those images, invert the images as indicated by inverters 103 in FIG. 2 and supply the inverted images to displays 65 which will display the corresponding images also during, those time intervals in which the chopper wheel 149 blocks the illuminating beam 135. At that time, the controller 57 controls the light shutter 141 to be switched into its light transmitting state such that the representations of orientation and will be perceived with a correct stereoscopic impression.

Summarized, a microscopy system method for inspecting a retina of an eye comprises generating an inverted intermediate image of the retina using an opthalmoscopic lens; detecting a left image of the intermediate image from a left viewing direction and detecting a right image of the intermediate image from a right viewing direction; and displaying an inverted representation of the detected left image to a right eye of a user and displaying an inverted representation of the detected right image to a left eye of the user.

The present invention has been described by way of exemplary embodiments to which it is not limited. Variations and modifications will occur to those skilled in the art without departing from the scope of the present invention as recited in the appended claims and equivalents thereof.

The invention claimed is:

1. A microscopy method comprising:
   operating a microscope in a first mode using an ophthalmoscopic lens disposed in a beam path between a first object and the microscope, the first mode comprising:
   generating an inverted intermediate image of the first object with the ophthalmoscopic lens,
   imaging the intermediate image onto a left image detector with a left beam portion of an imaging beam of the microscope and imaging the intermediate image onto a right image detector with a right beam portion of the imaging beam, and
   supplying an image detected by the left image detector and an image detected by the right image detector through first paths of switches to electronic image inverters for inversion;
   displaying an inverted representation of the image detected by the left image detector on a right display, and displaying an inverted representation of the image detected by the right image detector on a left display;
   switching from the first mode to a second mode by both removing the ophthalmoscopic lens from the beam path without requiring movement of other optical components into or out of the beam path and switching the switches from the first paths to second paths thereby bypassing the electronic image inverters; and
   operating the microscope in the second mode without using the ophthalmoscopic lens, the second mode comprising:
   imaging a second object onto the left image detector with the left beam portion and imaging the second object onto the right image detector with the right beam portion, and
   displaying a representation of an image detected by the left image detector on the left display, and displaying a representation of an image detected by the right image detector on the right display.

2. The microscopy method according to claim 1, wherein the left and right displays are included in a head mounted display.

3. The microscopy method according to claim 1, wherein the right display and the left display are the same in both the first mode and the second mode.

4. The microscopy method according to claim 3, wherein the right display and the left display are not moved when switching from the first mode to the second mode.

5. The microscopy method according to claim 4, wherein the right display and the left display maintain a same position relative to a user in both the first mode and the second mode.

6. The microscopy method according to claim 5, wherein the left and right displays are included in a head mounted display.

7. A microscopy method for inspecting a retina of an eye, the method comprising:
   generating, in a first mode of inspection, an inverted intermediate image of the retina; the first mode of inspection further comprising:
   detecting a left image of the intermediate image from a left viewing direction, and detecting a right image of the intermediate image from a right viewing direction;
   supplying the detected left image of the intermediate image and the detected right image of the intermediate image through first paths of switches to electronic image inverters thereby inverting the detected left image of the intermediate image and the detected right image of the intermediate image; and
   displaying a representation of the inverted left image of the intermediate image to a right eye of a user, and displaying a representation of the inverted right image of the intermediate image to a left eye of the user; and
   switching from the first mode of inspection and operating in a second mode of inspection in which the inverted intermediate image is temporarily not generated, the second mode of inspection further comprising:
   detecting a left image of the object from a left viewing direction and detecting a right image of the object from a right viewing direction, while the inverted intermediate image is not generated; and
   displaying a non-inverted representation of the detected left image to the left eye of the user and displaying a non-inverted representation of the detected right image to the right eye of the user,
   wherein, in the first mode of inspection, the intermediate image of the retina is generated by placing an ophthalmoscopic lens between the retina and the user, and wherein the switching from the first mode of inspection and operating in the second mode of inspection comprises both removing the ophthalmoscopic lens from between the retina and the user without requiring movement of other optical components into or out of the beam path and switching the switches from the first paths to second paths thereby bypassing the electronic image inverters.

8. The microscopy method according to claim 7, wherein the displaying of the representation of the inverted left image of the intermediate image to the right eye of the user is through a right display, and wherein the displaying of the representation of the inverted right image of the intermediate image to the left eye of the user is through a left display.

9. The microscopy method according to claim 8, wherein the displaying of the non-inverted representation of the detected left image to the left eye of the user is through the left display, and wherein the displaying of the non-inverted representation of the detected right image to the right eye of the user is through the right display.

10. The microscopy method according to claim 9, wherein the right display and the left display are the same in both the first mode of inspection and the second mode of inspection.

11. The microscopy method according to claim 10, wherein the right display and the left display are not moved when switching from the first mode of inspection and operating in the second mode of inspection.

12. The microscopy method according to claim 11, wherein the right display and the left display maintain a same position relative to the user in both the first mode of inspection and the second mode of inspection.

13. The microscopy method according to claim 12, wherein the right display and the left display are included in a head mounted display.

* * * * *

UNITED STATES PATENT AND TRADEMARK OFFICE
CERTIFICATE OF CORRECTION

PATENT NO. : 9,279,974 B2
APPLICATION NO. : 12/341581
DATED : March 8, 2016
INVENTOR(S) : Luecke et al.

It is certified that error appears in the above-identified patent and that said Letters Patent is hereby corrected as shown below:

Title page (73), under "Assignee", in Column 1, Line 1, delete "MEDITIC" and insert -- MEDITEC --, therefor.

(57), under "ABSTRACT", in Column 2, Line 3, delete "opthalmoscopic" and insert -- ophthalmoscopic --, therefor.

Specification

In Column 1, Line 48, delete "opthalmoscopic" and insert -- ophthalmoscopic --, therefor.

In Column 1, Lines 50-51, delete "opthalmoscopic" and insert -- ophthalmoscopic --, therefor.

In Column 1, Line 66, delete "opthalmoscopic" and insert -- ophthalmoscopic --, therefor.

In Column 2, Line 23, delete "opthalmoscopic" and insert -- ophthalmoscopic --, therefor.

In Column 2, Line 41, delete "opthalmoscopic" and insert -- ophthalmoscopic --, therefor.

In Column 2, Line 42, delete "opthalmoscopic" and insert -- ophthalmoscopic --, therefor.

In Column 2, Line 67, delete "opthalmoscopic" and insert -- ophthalmoscopic --, therefor.

In Column 3, Lines 3-4, delete "opthalmoscopic" and insert -- ophthalmoscopic --, therefor.

In Column 3, Line 29, delete "opthalmoscopic" and insert -- ophthalmoscopic --, therefor.

In Column 4, Line 4, delete "opthalmoscopic" and insert -- ophthalmoscopic --, therefor.

Signed and Sealed this
Twenty-sixth Day of July, 2016

Michelle K. Lee
*Director of the United States Patent and Trademark Office*

Specification

In Column 4, Line 7, delete "opthalmoscopic" and insert -- ophthalmoscopic --, therefor.

In Column 4, Line 10, delete "opthalmoscopic" and insert -- ophthalmoscopic --, therefor.

In Column 5, Line 23, delete "1 stands" and insert -- l stands --, therefor.

In Column 5, Line 33, delete "opthalmoscopic" and insert -- ophthalmoscopic --, therefor.

In Column 5, Line 35, delete "opthalmoscopic" and insert -- ophthalmoscopic --, therefor.

In Column 5, Line 41, delete "101l, 10r," and insert -- 101l, 101r, --, therefor.

In Column 5, Line 44, delete "651" and insert -- 65l --, therefor.

In Column 5, Line 49, delete "651" and insert -- 65l --, therefor.

In Column 5, Line 53, delete "opthalmoscopic" and insert -- ophthalmoscopic --, therefor.

In Column 5, Line 57, delete "651" and insert -- 65l --, therefor.

In Column 5, Line 62, delete "opthalmoscopic" and insert -- ophthalmoscopic --, therefor.

In Column 5, Line 63, delete "opthalmoscopic" and insert -- ophthalmoscopic --, therefor.

In Column 5, Line 64, delete "opthalmoscopic" and insert -- ophthalmoscopic --, therefor.

In Column 6, Line 15, delete "opthalmoscopic" and insert -- ophthalmoscopic --, therefor.

In Column 6, Line 27, delete "opthalmoscopic" and insert -- ophthalmoscopic --, therefor.

In Column 6, Line 29, delete "opthalmoscopic" and insert -- ophthalmoscopic --, therefor.

In Column 6, Line 41, delete "opthalmoscopic" and insert -- ophthalmoscopic --, therefor.

In Column 6, Line 51, delete "opthalmoscopic" and insert -- ophthalmoscopic --, therefor.

In Column 7, Line 12, delete "opthalmoscopic" and insert -- ophthalmoscopic --, therefor.